United States Patent
Sun et al.

(10) Patent No.: US 11,761,943 B1
(45) Date of Patent: Sep. 19, 2023

(54) CONFINING PRESSURE-ADJUSTABLE TEST AND OBSERVATION SYSTEM FOR SOIL DEFORMATION FEATURES DURING VACUUM PRELOADING AND TEST METHOD

(71) Applicants: Honglei Sun, Hangzhou (CN); Zili He, Hangzhou (CN); Jingling Lu, Hangzhou (CN); Zhenqi Weng, Hangzhou (CN); Jian Wu, Hangzhou (CN); Shao Yang, Hangzhou (CN); Wanjie Wang, Hangzhou (CN)

(72) Inventors: Honglei Sun, Hangzhou (CN); Zili He, Hangzhou (CN); Jingling Lu, Hangzhou (CN); Zhenqi Weng, Hangzhou (CN); Jian Wu, Hangzhou (CN); Shao Yang, Hangzhou (CN); Wanjie Wang, Hangzhou (CN)

(73) Assignee: Zhejiang University of Technology, Hangzhou (CN)

( * ) Notice: Subject to any disclaimer, the term of this patent is extended or adjusted under 35 U.S.C. 154(b) by 0 days.

(21) Appl. No.: 17/852,391

(22) Filed: Jun. 29, 2022

(51) Int. Cl.
*G01N 33/24* (2006.01)
*G01N 3/12* (2006.01)

(52) U.S. Cl.
CPC ............... *G01N 33/24* (2013.01); *G01N 3/12* (2013.01); *G01N 2203/0019* (2013.01); *G01N 2203/0284* (2013.01)

(58) Field of Classification Search
CPC .. G01N 33/24; G01N 3/12; G01N 2203/0019; G01N 2203/0284

USPC ............................................................ 73/784
See application file for complete search history.

(56) References Cited

U.S. PATENT DOCUMENTS

| 10,338,273 B2 * | 7/2019 | Wang | .................... | G01V 9/02 |
| 2016/0018380 A1 * | 1/2016 | Gerber-Siff | .......... | G01N 1/4077 |
| | | | | 73/61.59 |

FOREIGN PATENT DOCUMENTS

CN  108152151 A  *  6/2018  ............... G01N 3/02

OTHER PUBLICATIONS

Translation of Luo et al. CN-108152151-A (Year: 2018).*

* cited by examiner

*Primary Examiner* — Nathaniel T Woodward (57) ABSTRACT

Disclosed is a confining pressure-adjustable test and observation system for soil deformation features during vacuum preloading. The system includes a soil vacuum consolidation system, a vacuum drive system, a confining pressure system and a monitoring system; where the soil vacuum consolidation system includes a model box filled with test soil, the confining pressure system is arranged in the model box, two sides of the model box are provided with slide plates, and the slide plates on two sides are provided with expansion control cavities at two side ends of the model box correspondingly, and a corrugated air bag is arranged in the expansion control cavity and is connected to an external air pump and an air bag air pressure control device through a pipeline; the test soil in the model box is covered with geotextile, and the geotextile is covered with a vacuum film.

8 Claims, 10 Drawing Sheets

CONFINING PRESSURE-ADJUSTABLE TEST AND OBSERVATION SYSTEM FOR SOIL DEFORMATION FEATURES DURING VACUUM PRELOADING AND TEST METHOD

TECHNICAL FIELD

The present invention relates to a confining pressure-adjustable test and observation system for soil deformation features during vacuum preloading, and further relates to a test method using the confining pressure-adjustable test and observation system for soil deformation features during vacuum preloading.

BACKGROUND ART

A vacuum preloading drainage consolidation method, a common choice for soft soil foundation treatment these days, is extensively applied to soft soil foundation treatment of various projects such as coastal reclamation, airports and roads. It is still unclear about consolidation mechanisms of vacuum preloading and prefabricated drainage boards which are rare to utilize for improving high water content dredger fill (fluid soil). In addition, during vacuum preloading treatment of the high water content dredger fill, soil around the drainage boards can form dense "soil columns", which have high strength and low permeability, and hinder vacuum preloading as a result. In order to solve the problem of clogging caused by the soil columns, numerous scholars have theoretically analyzed its causes based on specific assumptions, and some have turned attention to different types of drainage boards. Nonetheless, there still lacks direct observation of exact causes of soil column formation during vacuum preloading currently. It is quite necessary to study formation of the soil columns visually for further study of their formation mechanisms and deformation laws of soil. To this end, the applicant applied for a patent for an invention Publication No, CN111537415A and entitled "Test System and Test Method for Observing Movement of Soil Particles during Vacuum Preloading" on Mar. 17, 2020, but the "Test System and Test Method for Observing Movement of Soil Particles during Vacuum Preloading" leads to inaccurate simulation of a real state in a test model due to confining pressure and groundwater in underground environment, and then results in insufficient accuracy of test data.

SUMMARY

For solving the technical problems, the present invention provides a confining pressure-adjustable test and observation system for soil deformation features during vacuum preloading. The system may more accurately simulate a real soil state, so as to more accurately and visually show formation causes of soil columns during vacuum preloading.

To this end, the confining pressure-adjustable test and observation system for soil deformation features during vacuum preloading provided by the present invention includes a soil vacuum consolidation system, a vacuum drive system, a confining pressure system and a monitoring system;

the soil vacuum consolidation system includes a model box filled with test soil, the model box being a rectangular box with an open top; a front side wall of the model box is provided with an observation window for observing movement of clay; the observation window is covered with a glass plate which fits same in size, the glass plate being provided with a marking point for marking a test result; a rear side wall of the model box is provided with a first sensor lead hole and a second sensor lead hole, a left side wall of the model box is provided with a vacuum pipeline port, and a support for fixing a plastic drainage board is arranged in the model box, the plastic drainage board being vertically fixed in the test soil through the support; and a top of the plastic drainage board is connected to a manual joint, a top of the manual joint being connected to a transverse connection pipe, the transverse connection pipe passing through the vacuum pipeline port to be connected to a vacuum pipeline; and the confining pressure system is arranged in the model box, two sides of the model box are provided with slide plates, pulleys are arranged at matching positions of an upper end and a lower end of the slide plates and a model box frame, slide rails are arranged at corresponding positions on the model box frame, inner sides of the slide plates are fixedly covered with elastic sealing cloth, edges around the elastic sealing cloth are pressed, through battens, against side walls of the model box to form a liquid seal, the slide plates on two sides are provided with expansion control cavities at two side ends of the model box correspondingly, and a foldable corrugated air bag is arranged in the expansion control cavity, end surfaces of two sides of the corrugated air bag being attached and fixed on an inner side wall of the model box and a side wall of the slide plate, and the corrugated air bag being connected to an external air pump and an air bag air pressure control device through a pipeline.

Preferably, the test and observation system includes a groundwater simulation system, the groundwater simulation system including a honeycomb water reservoir arranged at a bottom, the honeycomb water reservoir being connected, through a pipeline, to a vertically distributed transparent water storage bucket with height scales, and the honeycomb water reservoir being covered with a wire mesh, soil being arranged above the wire mesh.

Preferably, an interior of the model box is provided with a bottom frame plate, the lower slide rails are arranged on the bottom frame plate, a placement groove is provided below the bottom frame plate, and the honeycomb water reservoir is provided in the placement groove.

Preferably, a top edge of the model box is externally provided with a rectangular first sealing frame, an upper surface of the first sealing frame being connected to a second sealing frame through bolts; and the test soil is covered with geotextile, the geotextile is covered with a vacuum film, an outer edge of the vacuum film is sandwiched between the first sealing frame and the second sealing frame, and a sealing gasket is arranged between the vacuum film and the second sealing frame;

The vacuum drive system includes a vacuum water and air separation box for collecting water and air discharged from the model box, a vacuum jet pump for providing negative pressure, and a vacuum pressure control device for adjusting a vacuum load in the test system; a top of the vacuum water and air separation box is provided with a first connection port, a second connection port and a third connection port, the first connection port being connected to the model box through the vacuum pipeline, the second connection port being connected to the vacuum pressure control device, and the third connection port being connected to the vacuum jet pump; and a water outlet is provided on a lower side wall of the vacuum water and air separation box, the water outlet being externally connected to a drain pipe, the drain pipe being provided with a drain valve; and The monitoring system includes a pore water pressure sensor for monitoring water pressure change of a pore in soil during vacuum preloading, a vacuum gauge head for measuring a vacuum degree of soil at a bottom of the model box, a linear variable differential transformer (LVDT) displacement sensor for collecting surface settlement data of the test soil, a tracer particle for calculating a displacement field of the soil, and a high-definition camera for shooting and recording during a test; where a sensor fixing support is arranged at the top of the model box, the LVDT displacement sensor is fixed on the sensor fixing support, a camera support is arranged outside the observation window, and the high-definition camera is fixed on the camera support; the pore water pressure sensor is inserted into the first sensor lead hole from outside, and the pore water pressure sensor is buried in the test soil; the vacuum gauge head is inserted into the second sensor lead hole from outside, and the vacuum gauge head is buried in the test soil; and the high-definition camera is equipped with camera fixing aluminum rails to fix the camera in position, and LEDs are mounted around the model box to enhance brightness of a photo, and facilitate subsequent calculation.

Preferably, the glass plate of the observation window is made of acrylic plastic sheets for aircraft.

Preferably, the model box is made of aluminum plates, the guide rails are made of aluminum plates, the first sensor lead holes are staggered and spaced apart, and sealing plugs are arranged in the first sensor lead holes and the second sensor lead holes.

The present invention further relates to a test method using the confining pressure-adjustable test and observation system for soil deformation features during vacuum preloading, the method includes:

step 1, preparing a model:
determining quality of a soil sample required by a model box, and preparing the test soil sample; fixing a plastic drainage board at a set position through a support, mounting a vacuum pipeline, a pore water pressure sensor and a vacuum gauge head, spraying tracer particles on an inner side of an observation window, putting the prepared test soil sample into the model box, covering the test soil sample with geotextile and a vacuum film, and sealing the model box; and connecting the model box in a soil vacuum consolidation system to a vacuum drive system through the vacuum pipeline to guarantee airtightness of a whole test system;

step 2, debugging a system:
starting a data monitoring system, setting and adjusting data of the pore water pressure sensor and an LVDT displacement sensor, starting a vacuum pressure control device, observing readings of a vacuum gauge and the sensors, and guaranteeing correct data correspondence through zero setting; and mounting a high-definition camera on a camera fixing support, adjusting a field of view, and adjusting an aperture and a focal length to make the tracer particles to be imaged clearly in the field of view;

step 3, setting confining pressure:
starting an air pump, connecting the air pump to an air bag air pressure control device to pressurize an corrugated air hag until a set pressure is reached, and setting the confining pressure of soil through the set pressure;

step 4, performing vacuum preloading pumping and drainage:

starting the vacuum drive system to perform vacuum preloading pumping and drainage; and step 5, analyzing a test photo:
taking, through the high-definition camera, photos of the soil and the tracer particles in the field of vision during vacuum preloading during a test, and transmitted the photos to a computer for being processed through a data collection system; calculating a control point center of a calibration point used for converting an image and space coordinates; determining an analysis area, dividing the analysis area into a plurality of grids, calculating pixel coordinates of the grids in each frame image by using a correlation coefficient, filtering and analyzing output data by using the correlation coefficient, manually deleting incorrect output data, and converting the pixel coordinates into space coordinates to obtain information on deformation of the soil.

Preferably, in step 1, confining pressure of soil at a sampling position is measured while the model is prepared.

The present invention has the following technical effects:

(1) A test image measurement method of the present invention has high precision, may measure soil movement within a specified area, and has a high data resolution, and may carry out long-term continuous measurement.

(2) Test layout of the model of the present invention is similar to conditions of site construction, may simulate vacuum consolidation of the site soil well, and measure soil movement during the process, and test data have practical research significance.

(3) The pore water pressure sensors of the model of the present invention are closely arranged, and may match particle image velocimetry (PIV) data to obtain real-time information on the soil column.

(4) The model of the present invention may fix and place the high-definition camera, so as to reduce subsequent calculation errors caused by the fact that the camera is not fixed.

(5) The model of the present invention may guarantee desirable airtightness during the test process, may record and measure movement of soil particles, vertical displacement of soil surface, water pressure and vacuum degrees of the pores in the soil through cooperation with the pore water pressure sensor, a displacement meter, the vacuum gauge and a PTV measurement system, monitor the test process in real time, simulate the site construction of vacuum preloading, and therefore propose a better engineering practice solution.

(6) The corrugated air bag is pressurized by connecting the air pump to the air bag air pressure control device until the set pressure is reached, the confining pressure of the soil is set through the set pressure, especially, the slide plate with elastic sealing cloth may not only guarantee waterproof sealing, and create specific underground soil environment, but set the confining pressure by pressurizing the corrugated air bag, two end surfaces of the corrugated air bag are attached to the inner side walls of the slide plate and the model box, so the corrugated air bag may more accurately and effectively pressurize the slide plate, thus pressurizing two sides of the soil, and the confining pressure may be set through force conduction after the two sides of the soil is pressurized.

(7) The groundwater infiltration environment may be simulated by setting the honeycomb water reservoir below the soil. The honeycomb water reservoir infiltrates water into the soil, and the transparent water storage bucket connected to the honeycomb water reservoir adjusts a water head, thus adjusting water pressure.

DETAILED DESCRIPTION OF THE EMBODIMENTS

The present invention will be described in detail below with reference to accompanying drawings and in conjunction with embodiments. The same parts are denoted by the same reference numerals. It should be noted that the words "front", "back" "left", "right", "up" and "down" used in the following description refer to directions in the drawings, and the words "bottom" and "top", "inside" and "outside" separately refer to directions towards or away from geometric centers of specific parts.

With reference to FIGS. 1-9, a confining pressure-adjustable test and observation system for soil deformation features during vacuum preloading provided by the present invention includes a soil vacuum consolidation system, a vacuum drive system, a confining pressure system and a monitoring system.

The soil vacuum consolidation system includes a model box 1 filled with test soil, the model box 1 being a rectangular box with an open top. A front side wall of the model box 1 is provided with an observation window 2 for observing movement of clay. The observation window 2 is covered with a glass plate 3 which fits same in size, the glass plate 3 being provided with a marking point 4 for marking a test result. A rear side wall of the model box 1 is provided with a first sensor lead hole 5 and a second sensor lead hole 6, a left side wall of the model box 1 is provided with a vacuum pipeline port 7, and a support 9 for fixing a plastic drainage board 8 is arranged in the model box 1, the plastic drainage board 8 being vertically fixed in the test soil through the support 9. And a top of the plastic drainage board 8 is connected to a manual joint 10, a top of the manual joint 10 being connected to a transverse connection pipe 11, the transverse connection pipe 11 passing through the vacuum pipeline port 7 to be connected to a vacuum pipeline 12.

Figure 1:
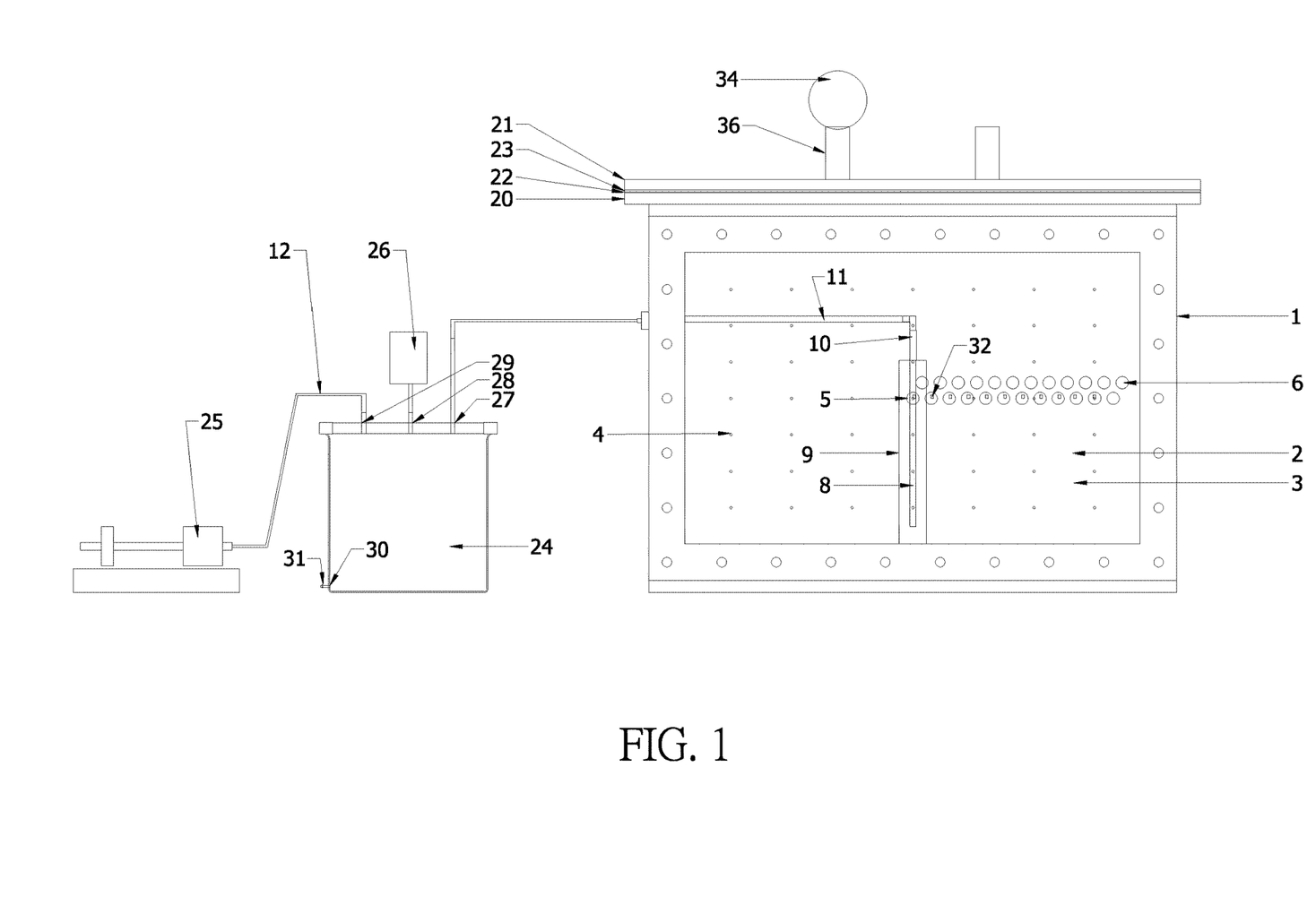
FIG. 1 is an overall schematic diagram of a confining pressure-adjustable test and observation system for soil deformation features during vacuum preloading provided by Embodiment 1 of the present invention.
Figure 2:
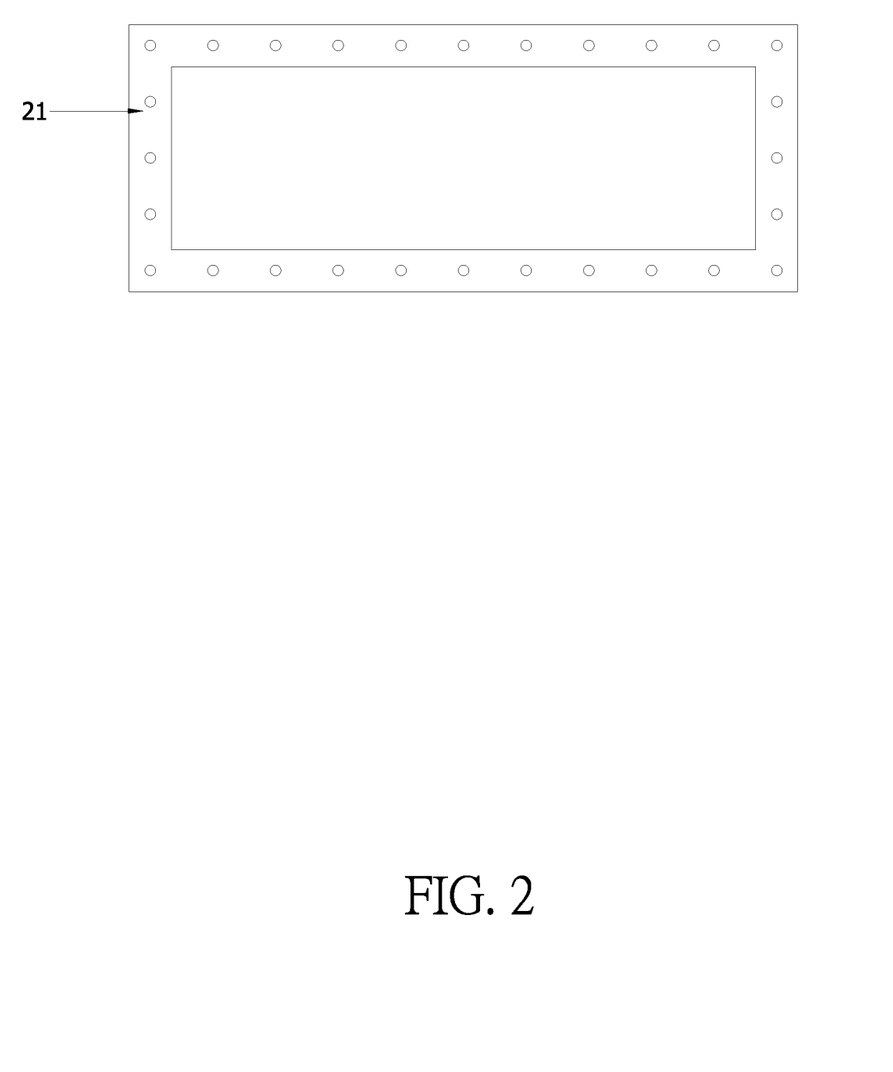
FIG. 2 is a schematic top view of a model box in FIG. 1.
Figure 3:
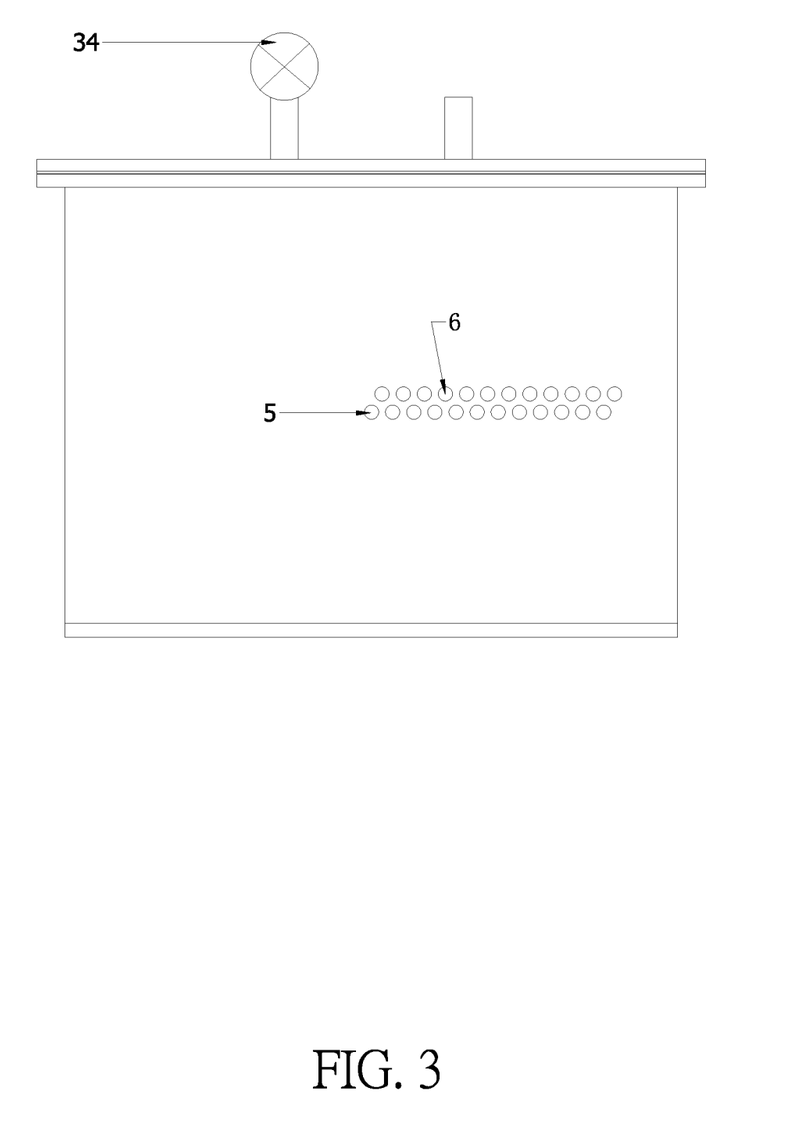
FIG. 3 is a schematic rear view of the model box in FIG. 1.
Figure 4:
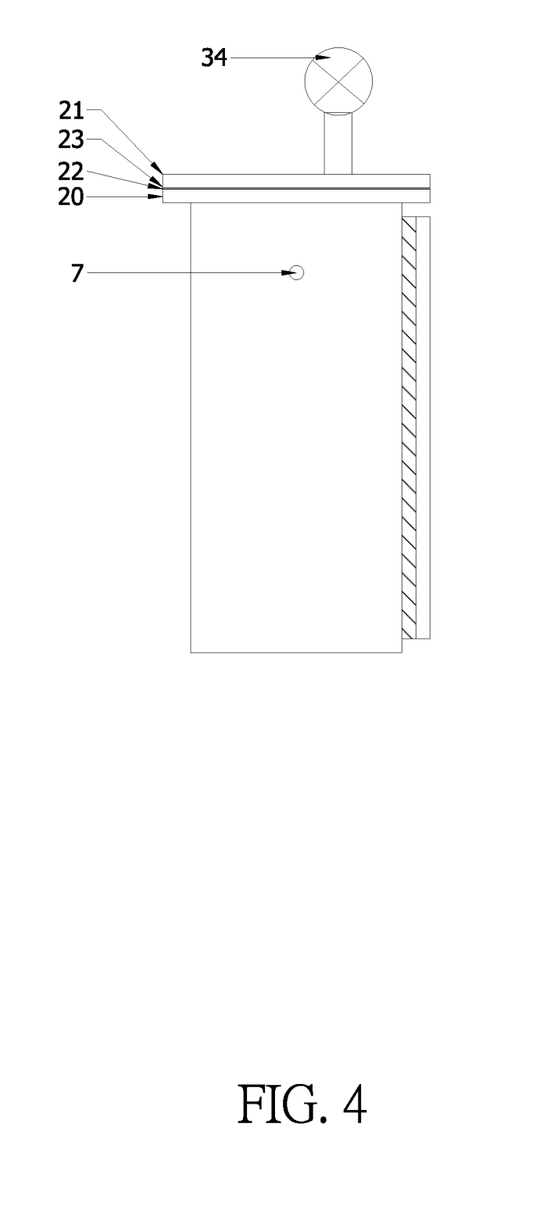
FIG. 4 is a schematic side view of the model box in FIG. 1.
Figure 5:
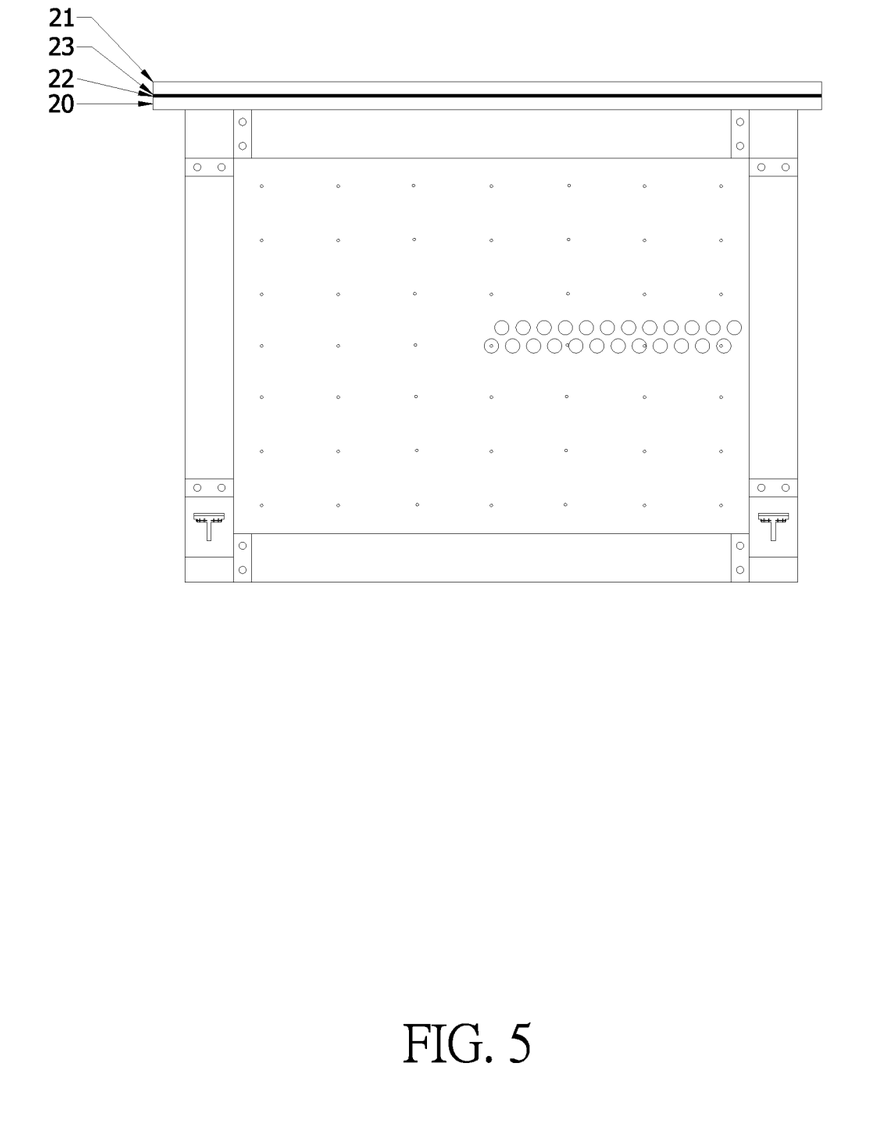
FIG. 5 is a structural schematic diagram of the model box, in FIG. 1, with camera fixing aluminum rails mounted on a frame bar on one side.
Figure 6:
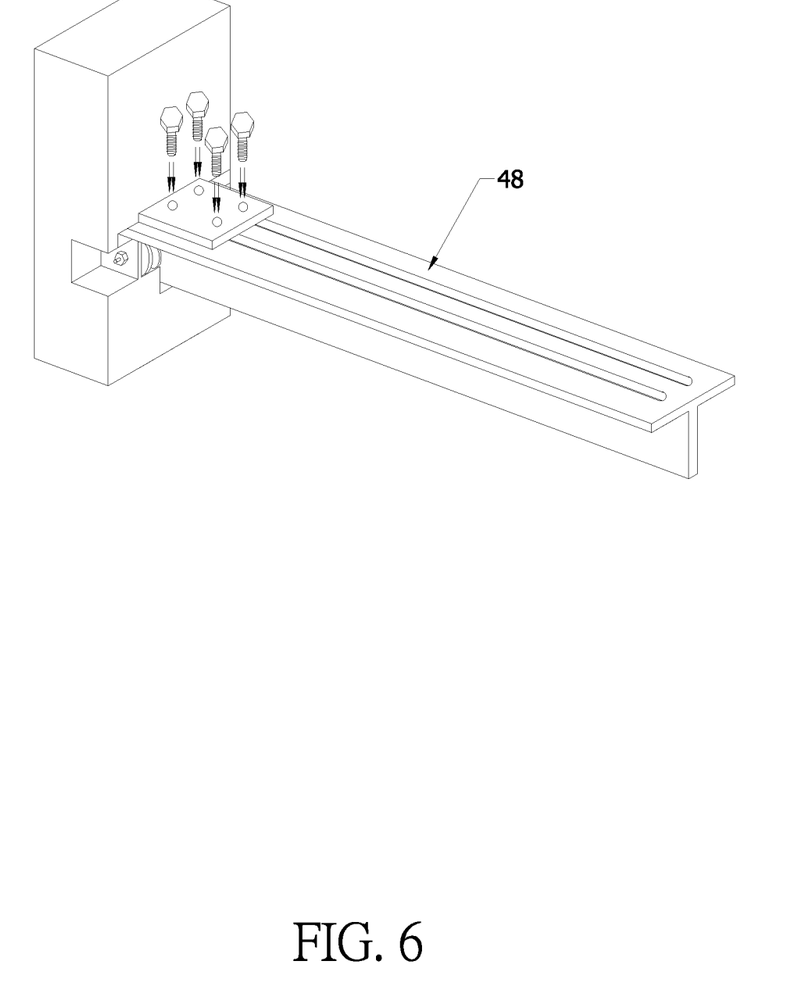
FIG. 6 is a structural schematic diagram of the frame bar on one side on which the camera fixing aluminum rails are mounted.
Figure 7:
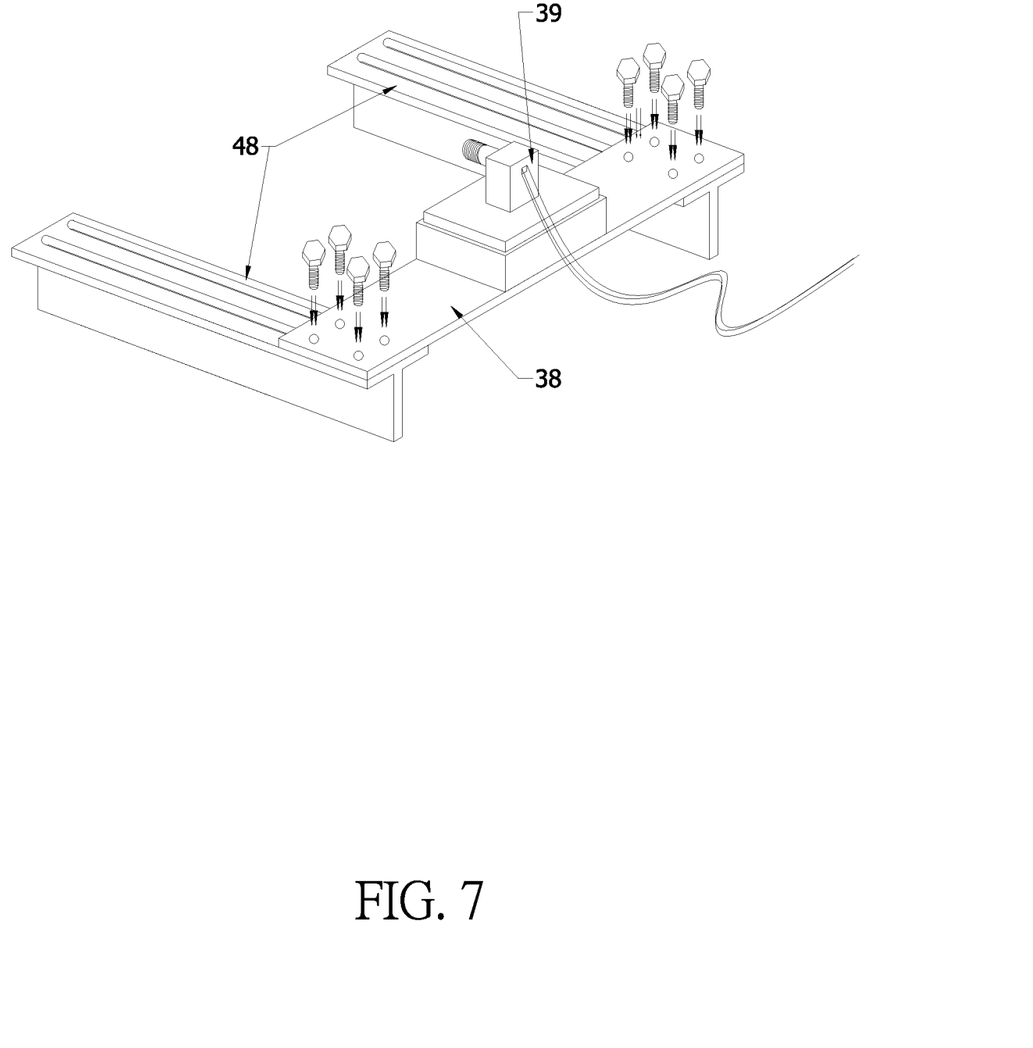
FIG. 7 is a structural schematic diagram of two sides of frame bars on which camera fixing aluminum rails are correspondingly mounted.
Figure 8:
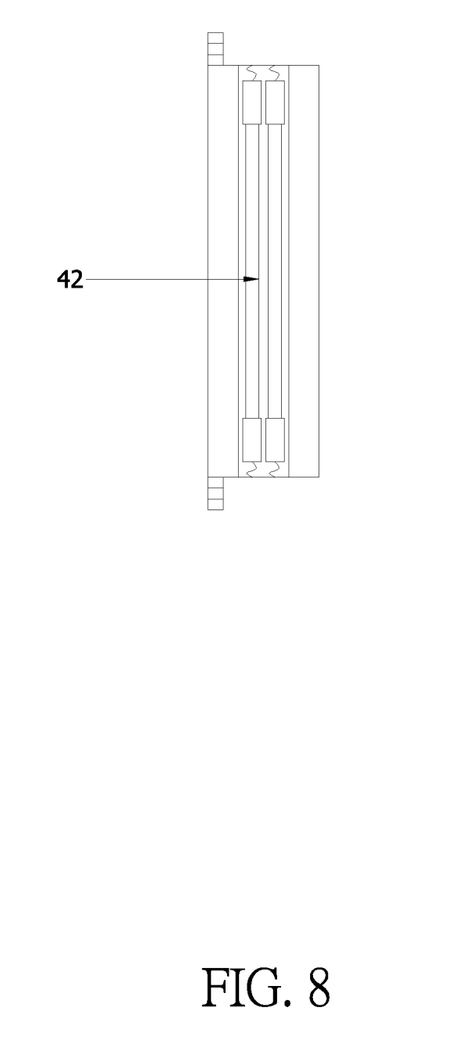
FIG. 8 is a structural diagram of the frame bar, provided with LEDs, of the model box in FIG. 6.
Figure 9:
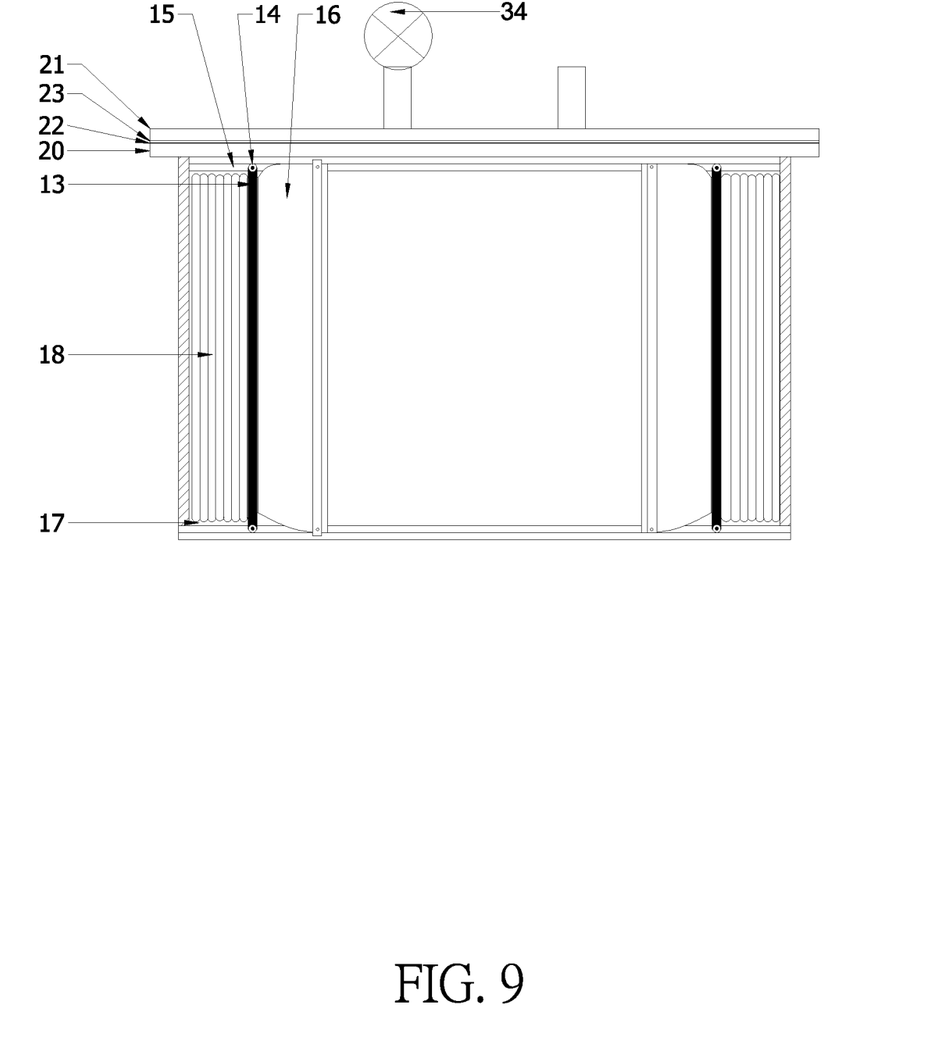
FIG. 9 is a structural schematic sectional view of the model box in FIG. 1.

The confining pressure system is arranged in the model box 1, two sides of the model box 1 are provided with slide plates 13, pulleys 14 are arranged at matching positions of an upper end and a lower end of the slide plates 13 and a model box frame, slide rails 15 are arranged at corresponding positions on the model box frame, inner sides of the slide plates 13 are fixedly covered with elastic sealing cloth 16, edges around the elastic sealing cloth 16 are pressed, through battens, against side walls of the model box 1 to form a liquid seal, the slide plates 13 on two sides are provided, through dividing, with expansion control cavities 17 at two side ends of the model box correspondingly, and a foldable corrugated air bag 18 is arranged in the expansion control cavity 17, end surfaces of two sides of the corrugated air bag 18 being attached and fixed on an inner side wall of the model box 1 and a side wall of the slide plate 13, and the corrugated air bag 18 being connected to an external air pump and an air bag air pressure control device through a pipeline. The air bag air pressure control devices usually include an air pump and an air pressure stabilization mechanism.

A top edge of the model box 1 is externally provided with a rectangular first sealing frame 20, an upper surface of the first sealing frame 20 being connected to a second sealing frame 21 through bolts. And the test soil is covered with geotextile, the geotextile is covered with a vacuum film 22, an outer edge of the vacuum film 22 is sandwiched between the first sealing frame 20 and the second sealing frame 21, and a sealing gasket 23 is arranged between the vacuum film 22 and the second sealing frame 21.

The vacuum drive system includes a vacuum water and air separation box 24 for collecting water and air discharged from the model box 1, a vacuum jet pump 25 for providing negative pressure, and a vacuum pressure control device 26 for adjusting a vacuum load in the test system. A top of the vacuum water and air separation box 24 is provided with a first connection port 27, a second connection port 28 and a third connection port 29, the first connection port 27 being connected to the model box 1 through the vacuum pipeline, the second connection port 28 being connected to the vacuum pressure control device 26, and the third connection port 29 being connected to the vacuum jet pump 25. And a water outlet 30 is provided on a lower side wall of the vacuum water and air separation box 24, the water outlet 30 being externally connected to a drain pipe, and the drain pipe being provided with a drain valve 31.

The monitoring system includes a pore water pressure sensor 32 for monitoring water pressure change of a pore in soil during vacuum preloading, a vacuum gauge head for measuring a vacuum degree of soil at a bottom of the model box 1, a linear variable differential transformer (LVDT) displacement sensor 34 for collecting surface settlement data of the test soil, a tracer particle for calculating a displacement field of the soil, and a high-definition camera 39 for shooting and recording during a test. A sensor fixing support 36 is arranged at the top of the model box 1, the LVDT displacement sensor 34 is fixed on the sensor fixing support 36, a camera support 38 is arranged outside the observation window 2, the glass plate 3 of the observation window 2 is made of organic aviation glass, and the high-definition camera 39 is fixed on the camera support. The pore water pressure sensor 32 is inserted into the first sensor lead hole 5 from outside, and the pore water pressure sensor 32 is buried in the test soil. The vacuum gauge head is inserted into the second sensor lead hole 6 from outside, and the vacuum gauge head is buried in the test soil. And the high-definition camera 39 is equipped with camera fixing aluminum rails 48 to fix the camera in position, and LEDs 42 are mounted around the model box 1 to enhance brightness of a photo, and facilitate subsequent calculation. The model box 1 is made of aluminum plates, the guide rails are made of aluminum plates, the first sensor lead holes 5 are staggered and spaced apart, and sealing plugs are arranged in the first sensor lead holes 5 and the second sensor lead holes 6.

With reference to FIGS. 1-9, the present invention provides a test method using the confining pressure-adjustable test and observation system for soil deformation features during vacuum preloading. The method includes:

step 1, a model is prepared:

Quality of a soil sample required by a model box 1 is determined firstly, and the test soil sample is prepared; a plastic drainage board 8 is fixed at a set position through a support, a vacuum pipeline, a pore water pressure sensor 32 and a vacuum gauge head are mounted, tracer particles are sprayed on an inner side of an observation window 2, the prepared test soil sample is put into the model box 1, the test soil sample is covered with geotextile and a vacuum film 22, and the model box 1 is sealed. And the model box 1 in a soil vacuum consolidation system is connected to a vacuum drive system through the vacuum pipeline to guarantee airtightness of a whole test system.

In step 1, confining pressure of soil at a sampling position is measured while the model is prepared.

Step 2, a system is debugged:

A data monitoring system is started, data of the pore water pressure sensor 32 and an LVDT displacement sensor 34 are set and adjusted, a vacuum pressure control device 26 is started, readings of a vacuum gauge and the sensors are observed, and correct data correspondence through zero setting is guaranteed. A high-definition camera 39 is mounted on a camera fixing support, a field of view is adjusted, and an aperture and a focal length are adjusted to make the tracer particles to be imaged clearly in the field of view.

Step 3, confining pressure is set:

An air pump is started, the air pump is connected to an air bag air pressure control device to pressurize an corrugated air bag 18 until a set pressure is reached, and the confining pressure of soil is set through the set pressure.

Step 4, vacuum preloading pumping and drainage are performed:

The vacuum drive system is started to perform vacuum preloading pumping and drainage.

Step 5, a test photo is analyzed:

Through the high-definition camera 39, photos of the soil and the tracer particles are taken in the field of vision during vacuum preloading during a test, and the photos are transmitted to a computer for being processed through a data collection system. A control point center of a calibration point used for converting an image and space coordinates is calculated firstly. An analysis area is determined, the analysis area is divided into a plurality of grids, pixel coordinates of the grids m each frame image are calculated by using a correlation coefficient, output data are filtered and analyzed by using the correlation coefficient, incorrect output data are manually deleted, and the pixel coordinates are converted into space coordinates finally to obtain information on deformation of the soil.

Figure 10:
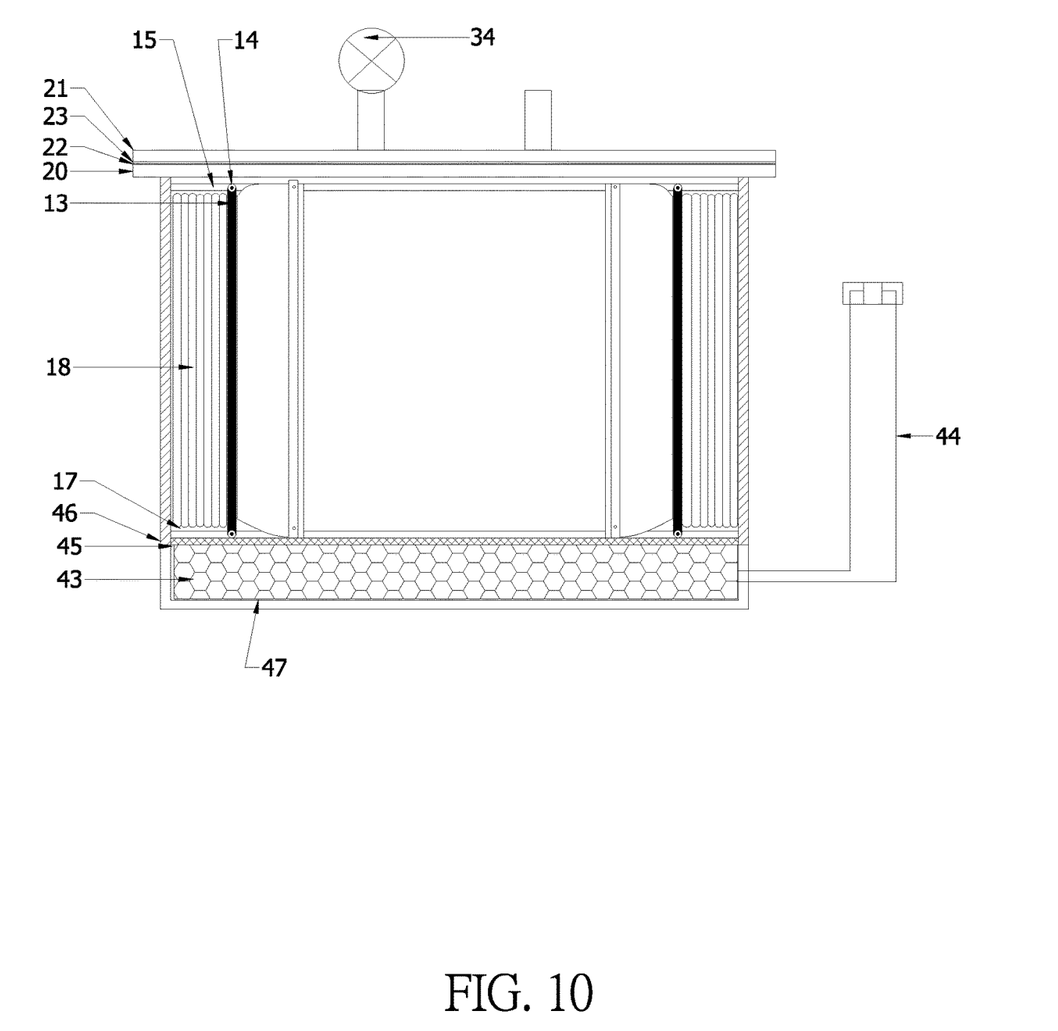
FIG. 10 is a structural schematic sectional view of a model box provided in Embodiment 2 of the present invention.

With reference to FIG. 10, Embodiment 2 of the present invention is basically the same as Embodiment 1 except that the test and observation system includes a groundwater simulation system, the groundwater simulation system including a honeycomb water reservoir 43 arranged at a bottom, the honeycomb water reservoir 43 being connected, through a pipeline, to a vertically distributed transparent water storage bucket 44, the transparent water storage bucket. 44 being provided with height scales. The honeycomb water reservoir 43 is covered with a wire mesh 45, and soil is arranged above the wire mesh 45. An interior of the model box 1 is provided with a bottom frame plate 46, the lower slide rails 15 are arranged on the bottom frame plate 46, a placement groove 47 is provided below the bottom frame plate 46, and the honeycomb water reservoir 43 is provided in the placement groove 47. The honeycomb water reservoir 47 may simulate groundwater, and the transparent water storage bucket 44 connected to the honeycomb water reservoir 43 adjusts a water head, thus adjusting water pressure, and improving the accuracy of the test.

What is described above is merely the preferred embodiment of the present invention, the protection scope of the present invention is not limited to the above embodiments, but all technical solutions under the idea of the present invention shall fall within the protection scope of the present invention. It shall be noted that several improvements and polishing made by those of ordinary skill in the art on the premise without deviating from a principle of the present invention shall be integrated as falling within the protection scope of the present invention.

What is claimed is:

1. A confining pressure-adjustable test and observation system for soil deformation features during vacuum preloading, comprising a soil vacuum consolidation system, a vacuum drive system, a confining pressure system and a monitoring system; wherein the soil vacuum consolidation system comprises a model box filled with test soil, the model box being a rectangular box with an open top; a front side wall of the model box is provided with an observation window for observing movement of clay; the observation window is covered with a glass plate which fits same in size, the glass plate being provided with a marking point for marking a test result; a rear side wall of the model box is provided with a first sensor lead hole and a second sensor lead hole, a left side wall of the model box is provided with a vacuum pipeline port, and a support for fixing a plastic drainage board is arranged in the model box, the plastic drainage board being vertically fixed in the test soil through the support; and a top of the plastic drainage board is connected to a manual joint, a top of the manual joint being connected to a transverse connection pipe, the transverse connection pipe passing through the vacuum pipeline port to be connected to a vacuum pipeline; and the confining pressure system is arranged in the model box, two sides of the model box are provided with slide plates, pulleys are arranged at matching positions of an upper end and a lower end of the slide plates and a model box frame, slide rails are arranged at corresponding positions on the model box frame, inner sides of the slide plates are fixedly covered with elastic sealing cloth, edges around the elastic sealing cloth are pressed, through battens, against side walls of the model box to form a liquid seal, the slide plates on two sides are provided with expansion control cavities at two side ends of the model box correspondingly, and a foldable corrugated air bag is arranged in the expansion control cavity, end surfaces of two sides of the corrugated air bag being attached and fixed on an inner side wall of the model box and a side wall of the slide plate, and the corrugated air bag being connected to an external air pump and an air bag air pressure control device through a pipeline.

2. The confining pressure-adjustable test and observation system for soil deformation features during vacuum preloading according to claim 1, comprising a groundwater simulation system, the groundwater simulation system comprising a honeycomb water reservoir arranged at a bottom, the honeycomb water reservoir being connected, through a pipeline, to a vertically distributed transparent water storage bucket with height scales, and the honeycomb water reservoir being covered with a wire mesh, soil being arranged above the wire mesh.

3. The confining pressure-adjustable test and observation system for soil deformation features during vacuum preloading according to claim 2, wherein an interior of the model box is provided with a bottom frame plate, the lower slide rails are arranged on the bottom frame plate, a placement groove is provided below the bottom frame plate, and the honeycomb water reservoir is provided in the placement groove.

4. The confining pressure-adjustable test and observation system for soil deformation features during vacuum preloading according to claim 1, wherein a top edge of the model box is externally provided with a rectangular first sealing frame, an upper surface of the first sealing frame being connected to a second sealing frame through bolts; and the test soil is covered with geotextile, the geotextile is covered with a vacuum film, an outer edge of the vacuum film is sandwiched between the first sealing frame and the second sealing frame, and a sealing gasket is arranged between the vacuum film and the second sealing frame;

the vacuum drive system comprises a vacuum water and air separation box for collecting water and air discharged from the model box, a vacuum jet pump for providing negative pressure, and a vacuum pressure control device for adjusting a vacuum load in the test system; a top of the vacuum water and air separation box is provided with a first connection port, a second connection port and a third connection port, the first connection port being connected to the model box through the vacuum pipeline, the second connection port being connected to the vacuum pressure control device, and the third connection port being connected to the vacuum jet pump; and a water outlet is provided on a lower side wall of the vacuum: water and air separation box, the water outlet being externally connected to a drain pipe, the drain pipe being provided with a drain valve; and the monitoring system comprises a pore water pressure sensor for monitoring water pressure change of a pore in soil during vacuum preloading, a vacuum gauge head for measuring a vacuum degree of soil at a bottom of the model box, a linear variable differential transformer (LVDT) displacement sensor for collecting surface settlement data of the test soil, a tracer particle for calculating a displacement field of the soil, and a high-definition camera for shooting and recording during a test; wherein a sensor fixing support is arranged at the top of the model box, the LNDT displacement sensor is fixed on the sensor fixing support, a camera support is arranged outside the observation window, and the high-definition camera is fixed on the camera support; the pore water pressure sensor is inserted into the first sensor lead hole from outside, and the pore water pressure sensor is buried in the test soil; the vacuum gauge head is inserted into the second sensor lead hole from outside, and the vacuum gauge head is buried in the test soil; and the high-definition camera is equipped with camera fixing aluminum rails to fix the camera in position, and LEDs are mounted around the model box to enhance brightness of a photo, and facilitate subsequent calculation.

5. The confining pressure-adjustable test and observation system for soil deformation features during vacuum preloading according to claim 4, wherein the glass plate of the observation window is made of acrylic plastic sheets for aircraft.

6. The confining pressure-adjustable test and observation system for soil deformation features during vacuum preloading according to claim 4, wherein the model box is made of aluminum plates, the guide rails are made of aluminum plates, the first sensor lead holes are staggered and spaced apart, and sealing plugs are arranged in the first sensor lead holes and the second sensor lead holes.

7. A test method of the confining pressure-adjustable test and observation system for soil deformation features during vacuum preloading according to claim 4, comprising:

step 1, preparing a model:

determining quality of a soil sample required by a model box, and preparing the test soil sample; fixing a plastic drainage board at a set position through a support, mounting a vacuum pipeline, a pore water pressure sensor and a vacuum gauge head, spraying tracer particles on an inner side of an observation window, putting the prepared test soil sample into the model box, covering the test soil sample with geotextile and a vacuum film, and sealing the model box; and connecting the model box in a soil vacuum consolidation system to a vacuum drive system through the vacuum pipeline to guarantee airtightness of a whole test system;

step 2, debugging a system:

starting a data monitoring system, setting and adjusting data of the pore water pressure sensor and an LVDT displacement sensor, starting a vacuum pressure control device, observing readings of a vacuum gauge and the sensors, and guaranteeing correct data correspondence through zero setting; and mounting a high-definition camera on a camera fixing support, adjusting a field of view and adjusting an aperture and a focal length to make the tracer particles to be imaged clearly in the field of view;

step 3, setting confining pressure:

starting an air pump, connecting the air pump to an air bag air pressure control device to pressurize a corrugated air bag until a set pressure is reached, and setting the confining pressure of soil through the set pressure;

step 4, performing vacuum preloading pumping and drainage:

starting the vacuum drive system to perform vacuum preloading pumping and drainage; and step 5, analyzing a test photo:

taking, through the high-definition camera, photos of the soil and the tracer particles in the field of vision during vacuum preloading during a test, and transmitted the photos to a computer for being processed through a data collection system; calculating a control point center of a calibration point used for converting an image and space coordinates; determining an analysis area, dividing the analysis area into a plurality of grids, calculating pixel coordinates of the grids in each frame image by using a correlation coefficient, filtering and analyzing output data by using the correlation coefficient, manually deleting incorrect output data, and converting the pixel coordinates into space coordinates to obtain information on deformation of the soil.

8. The test method of the confining pressure-adjustable test and observation system for soil deformation features during vacuum preloading according to claim 7, wherein in step 1, confining pressure of soil at a sampling position is measured while the model is prepared.

\* \* \* \* \*